(12) United States Patent
Donner et al.

(10) Patent No.: US 8,648,601 B2
(45) Date of Patent: Feb. 11, 2014

(54) METHOD FOR CONTROL OF STABILIZER ADDITIVES IN ELECTROLESS METAL AND METAL ALLOY PLATING ELECTROLYTES

(75) Inventors: Constanze Donner, Berlin (DE); Guenther Bauer, Berlin (DE); Therese Stern, Berlin (DE); Kay Wurdinger, Berlin (DE); Lutz Brandt, Berlin (DE); Frank Bruening, Berlin (DE)

(73) Assignee: Atotech Deutschland GmbH, Berlin, DE (US)

(*) Notice: Subject to any disclaimer, the term of this patent is extended or adjusted under 35 U.S.C. 154(b) by 272 days.

(21) Appl. No.: 13/130,315

(22) PCT Filed: Nov. 24, 2009

(86) PCT No.: PCT/EP2009/065742
§ 371 (c)(1),
(2), (4) Date: May 20, 2011

(87) PCT Pub. No.: WO2010/060906
PCT Pub. Date: Jun. 3, 2010

(65) Prior Publication Data
US 2011/0221445 A1    Sep. 15, 2011

(30) Foreign Application Priority Data
Nov. 26, 2008  (EP) .................................. 08075906

(51) Int. Cl.
*G01N 27/42* (2006.01)
(52) U.S. Cl.
USPC ........ 324/425; 324/713; 324/158.1; 205/775; 205/794; 204/434; 427/304; 427/305; 427/306; 427/8

(58) Field of Classification Search
USPC ........... 324/713, 158.1; 427/304, 305, 306, 8, 427/437, 443.1; 204/434; 205/775, 794
See application file for complete search history.

(56) References Cited

U.S. PATENT DOCUMENTS

| | | | |
|---|---|---|---|
| 4,814,197 A * | 3/1989 | Duffy et al. ....................... 427/8 |
| 5,755,954 A | 5/1998 | Ludwig et al. |
| 2003/0201191 A1* | 10/2003 | Kovarsky et al. ............. 205/775 |
| 2005/0183958 A1 | 8/2005 | Wikiel et al. |
| 2007/0007148 A1* | 1/2007 | Okada et al. .................. 205/775 |
| 2007/0158210 A1* | 7/2007 | Stromereder et al. ........ 205/775 |
| 2007/0292615 A1* | 12/2007 | Dordi et al. .................. 427/299 |
| 2008/0197022 A1* | 8/2008 | Suzuki et al. ................. 205/775 |
| 2008/0264801 A1* | 10/2008 | West et al. .................... 205/775 |
| 2009/0101523 A1* | 4/2009 | Deng ......................... 205/777.5 |

OTHER PUBLICATIONS

V.N. Kuznetsov et al.; Electrochemical Study of the Electroless Copper Plating Process; Surface and Coatings Technology, 28 (1986) 151-160.

(Continued)

*Primary Examiner* — Huy Q Phan
*Assistant Examiner* — Temilade S Rhodes-Vivour
(74) *Attorney, Agent, or Firm* — Renner, Otto, Boisselle & Sklar, LLP

(57) ABSTRACT

The present invention describes a method for the measurement of the stabilizer additive concentration in electroless metal and metal alloy plating electrolytes comprising a voltammetric measurement. Said method comprises the steps a. conditioning of the working electrode, b. interaction of intermediates on the working electrode, c. measurement of the Faradaic current and d. determining the Faradaic current.

12 Claims, 10 Drawing Sheets

(56) References Cited

OTHER PUBLICATIONS

M. Paunovic; An Electrochemical Control System for Electroless Copper Bath; vol. 127, No. 2 . J. Electrochem. Soc.: Electrochemical Science and Technology, Feb. 1980; pp. 365-369.

D. Vitkavage et al.; Electroless Copper Deposition: Limiting Conditions and Accelerating-Inhibiting Effects; Annual Technical Conference Proceedings—American Electroplaters Society (1982), 69th, Paper A-5, 26 pp.

N. Sato et al.; AC Impedance and Coulostatic Studies on Electrochemical Detection of 2-Mercaptobenzothiazole in a Copper Electroless Plating Bath; J. Electrochem. Soc.: Electrochemical Science and Technology, Jul. 1988; pp. 1645-1650.

M.L. Rothstein; Square-Wave Voltammetry for Plating Solution Analyses; Metal Finishing, Oct. 1984, pp. 35-39.

G.O. Mallory et al; Electroless Plating: Fundamentals and Applications; pp. 34-37.

van der Putten et al.; Anisotropic Deposition of Electroless Nickel; J. Electrochem. Soc. vol. 140, No. 8, Aug. 1993; pp. 2229-2235.

C.A. Deckert; Electroless Copper Plating; ASM Handbook; vol. 5 Surface Engineering; 1994, 4 pages.

PCT/EP2009/065742; PCT International Search Report dated Mar. 2, 2010.

* cited by examiner

METHOD FOR CONTROL OF STABILIZER ADDITIVES IN ELECTROLESS METAL AND METAL ALLOY PLATING ELECTROLYTES

FIELD OF THE DISCLOSURE

The present invention describes a method to control the concentration of stabilizer additives in electroless metal and metal alloy plating electrolytes utilizing a voltammetric measurement.

BACKGROUND OF THE INVENTION

Electroless metal and metal alloy plating electrolytes usually comprise one or more sources of the metal(s) to be deposited in an ionic form, reducing agents, complexing agents, pH modifiers, accelerators and one or more stabilizer additives. The stabilizer additives stabilize such plating electrolytes against various manifestations of undesired plateout. In real life plating electrolytes, usually a mixture of several stabilizer agents is used at once in order to reach the desired electrolyte stability. Understanding their optimal replenishment rate is key to successful operation of electroless plating electrolytes. The stabilizer additives are usually employed at low concentrations, typically 1 to 100 ppm. Rapid changes of the chemistry of an operating electroless plating electrolyte may occur. Therefore, analysis and control of said stabilizer additives or stabilizer additive mixtures is a complex task.

Kuznetsov et al. compares the influence of different stabilizer components and additives including $K_3Fe(CN)_6$, mercaptobenzthiazol and 4-benzoylpyridin in a formaldehyde and EDTA based electroless copper electrolyte by a chrono-potentiometric method (Surface and Coatings Technology, 28 (1996) 151-160). This method is a currentless method following the potential-time evolution at mixed potential. Solely, discussed is the influence of different additives on the induction period before the autocatalytic copper deposition. However, no concentration dependence of the various additives on the chrono-potentiometric signals was shown.

Paunovic describes a modified chrono-potentiometric method and its application to an electroless copper electrolyte with formaldehyde as reducing agent (J. Electrochem. Soc., 127 (1980) 365-369). A change of the electrode potential at a constant applied current is recorded as a function of time. This method can be used by applying a cathodic as well as anodic constant current. Applying a cathodic current the overpotential shifts into cathodic direction with time until electrolyte decomposition starts due to depletion of copper ions. Applying an anodic current the overpotential shifts into anodic direction with time due to depletion of formaldehyde molecules. This time period between two constant potentials, called transition time, depends on the applied current density. If adsorption reduces the redox active electrode area and leads consequently to an increase of current density, the transition time decreases. This dependence can be used to determine the concentration of surface active additives. This investigation reveals an influence of the concentration of various stabilizer additives, e.g., mercaptobenzothiazole and NaCN on the transition time in cathodic and anodic chrono-potentiometry.

Vitkavage and Paunovic (Annual Technical Conference Proceedings-American Electroplaters' Society (1992), 69th (1), paper A-5, pp. 1-26) investigated the influence of various additive concentrations on copper reduction in an EDTA based electroless copper electrolyte. The authors revealed that with increasing additive concentrations the copper reduction current decreases, depending on the surface activities of the additives and various stirring conditions. This observation is also true for cyanide components as stabilizers. The applied potential run was applied without establishing stationary surface conditions prior the run.

Results from electrochemical impedance spectroscopy (EIS) and coulostatic measurements of an EDTA based electroless copper electrolyte are presented by Sato and Suzuki (J. Electrochem. Soc. 135 (1988) 1645-1650). The concentration of the stabilizer additive 2-mercaptobenzothiazole on platinum electrodes was determined by evaluating the double layer capacities as well as polarization resistances. The polarization resistance arises from electroless formaldehyde oxidation reduced by oxygen. With decreasing additive concentration decreases the polarization resistance. During all measurements no copper deposition occurred.

Rothstein describes a method to determine different additives in various plating electrolytes including mercaptobenzothiazole in an electroless copper electrolyte by square wave voltammetry (M. L. Rothstein, Metal Finishing 1984, October issue, 35-39). A squarewave is superimposed on the linear potential staircase sweep. The current is measured at the end of each half-wave, just prior to potential change. The reduction or oxidation currents of additives is measured directly without preadsorbing steps. The additives have to be oxidized or reduced itself.

The U.S. Pat. No. 4,814,197 discloses methods of analyzing and controlling an electroless plating solution comprising formaldehyde as the reducing agent. The methods also include a procedure for monitoring cyanide ions as stabilizer additive with a cyanide ion sensitive electrode wherein the potential between said $CN^-$-sensitive electrode and a Ag/AgCl reference electrode is measured. Such methods fail in the presence of a reducing agent like formaldehyde (see Example 4 of this invention).

A cyclic voltammtry study (A. M. T. van der Putten, J.-W. G. de Bakker, J. Electrochem. Soc., Vol. 140, No. 8, 1993, 2229-2235) describes the influence of $Pb^{2+}$ and thiourea stabilizer additives in an electroless nickel bath with hypophosphite as reducing agent on anisotropic nickel plating (bevel plating). The study does not mention attempts to extract the concentration of said stabilizer additives from the corresponding measurements.

The European patent application EP 0 265 901 A2 discloses a method for analyzing an electroless plating solution. The method utilizes a cyanide sensing electrode to determine the cyanide ion stabilizer concentration and a voltammetric method to determine the concentration of other stabilizer agents. The voltammetric method for measuring stabilizer concentrations comprises the steps of a) electrically float and equilibrate the electrodes to assume the mixed potential $E_{mix}$ and b) apply a positive sweep potential increasing the measured potential to a value above $E_{mix}$. From step b) concentration data of stabilizers are determined by measuring the shift of the peak potential of the plating bath in comparison to a defined reference standard potential, i.e., with the assumption that the peak plating bath potential is a function of the stabilizer agent(s) concentration. By this method only the potential peak position is used to determine the stabilizer concentration without taking into account that the stabilizer concentration is a function of the potential peak position and the current height at the potential peak position. Therefore two parameters are changed in parallel which are not independent of each other and whereas only one parameter is analyzed.

However, by using a combination of both potential peak position and current height at potential peak position a much more accurate determination of the stabilizer concentration can be derived.

In addition the use of a cyanide sensing electrode for measuring the cyanide ion stabilizer concentration in a chemical plating bath does not lead to reproducible results (see Example 4 of the current application).

The patent application US 2003/0201191 A1 discloses a voltammetric method for measuring the concentration of additives in a plating solution wherein the additive concentration is obtained by a ratio of the stripping peak area from the profile of the anodic current to a stripping peak area of a base solution.

The patent document JP 53009235 discloses an electrochemical method for determining the metal ion concentration in an electroless copper coating solution. The potential of the working electrode is changed periodically in this method.

The patent document JP 53009233 discloses an electrochemical method for control of copper electroless coating solution concentration wherein the current of a working electrode is changed periodically.

Thus, there is still a need for a reliable method which allows the measurement and control of a stabilizer additive or mixtures of stabilizer additives in electroless plating electrolytes, especially during use of said plating electrolytes.

OBJECT OF THE INVENTION

Therefore, it is the object of the present invention to provide a method for control of stabilizer additives and/or mixtures of stabilizer additives in electroless metal and metal alloy plating electrolytes. More particularly, the method should be reproducible and flexible in terms of stabilizer additive(s) and reducing agent(s) present in the electroless plating electrolyte. Such a method should be capable also of an on-line analysis of stabilizer additives during usage of said electroless plating electrolytes, e.g., provide real time control of the electroless plating electrolyte.

DETAILED DESCRIPTION OF THE INVENTION

The invention is related to a voltammetric method for control of stabilizer additives in electroless metal and metal alloy plating electrolytes. Said electrolytes comprise one or more sources of the metal or metal alloys to be deposited, reducing agent(s), complexing agent(s) and stabilizer additives. Examples for metals and metal alloys which can be deposited by electroless plating processes are copper, nickel, gold, palladium, ruthenium, tin, silver and alloys containing at least one of said metals. Electroless plating methods comprise autocatalytic, cementation and immersion processes. The inventive voltammetric method to control the concentration of stabilizer additives is suitable for any kind of electroless plating electrolytes.

Such electroless plating electrolytes comprise for example a source of copper ions, pH modifiers, complexing agents such as EDTA, alkanol amines or tartrate salts, accelerators, stabilizer additives and a reducing agent. In most cases formaldehyde is used as reducing agent, other common reducing agents are hypophosphite, dimethylamine borane and borohydride. Typical stabilizer additives for electroless copper plating electrolytes are compounds such as mercaptobenzothiazole, thiourea, various other sulphur compounds, cyanide and/or ferrocyanide and/or cobaltocyanide salts, polyethyleneglycol derivatives, heterocyclic nitrogen compounds, methyl butynol, and propionitrile. In addition, molecular oxygen is often used as a stabilizer additive by passing a steady stream of air through the copper electrolyte (ASM Handbook, Vol. 5: Surface Engineering, pp. 311-312).

Another important example for electroless metal and metal alloy plating electrolytes are compositions for deposition of nickel and alloys thereof. Such electrolytes are usually based on hypophosphite compounds as reducing agent and further contain mixtures of stabilizer additives which are selected from the group comprising compounds of Group VI elements (S, Se, Te), oxo-anions ($AsO_2^-$, $IO_3^-$, $MoO_4^{2-}$), heavy metal cations ($Sn^{2+}$, $Pb^{2+}$, $Hg^+$, $Sb^{3+}$) and unsaturated organic acids (maleic acid, itaconic acid) (Electroless Plating: Fundamentals and Applications, Eds.: G. O. Mallory, J. B. Hajdu, American Electroplaters and Surface Finishers Society, Reprint Edition, pp. 34-36).

The voltammetric method for the measurement of the stabilizer additive concentration in electroless metal or metal alloy plating electrolytes, comprising the following steps:

a. conditioning of the working electrode surface b. thereafter bringing into contact such working electrode surface with the electroless metal or metal alloy plating electrolyte and applying a fixed potential to said working electrode surface c. measuring the Faradaic current by applying a potential scan starting from the fixed potential applied during step b d. determining of at least one Faradaic current value at least one potential value of a potential scan.

Figure 1:
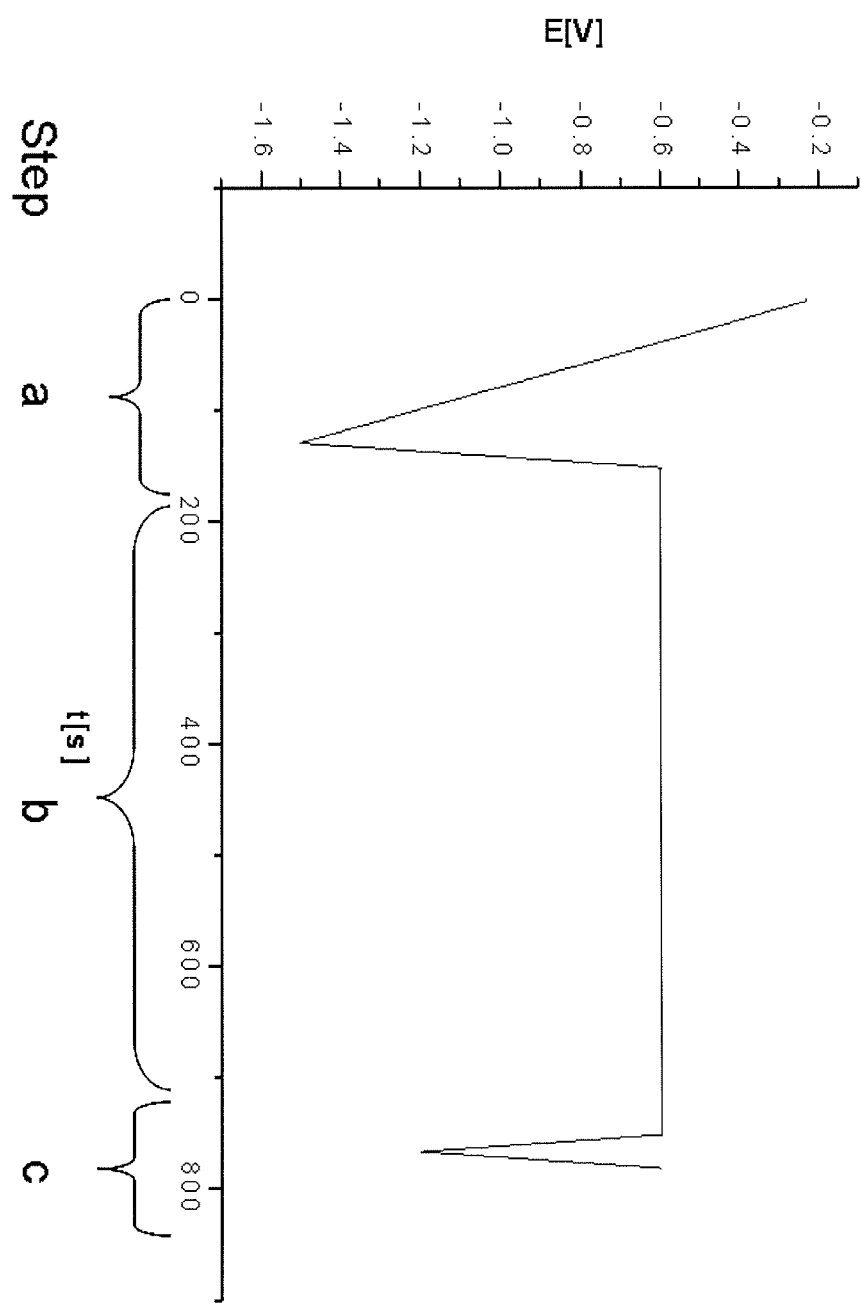
FIG. 1: The potential course applied at the electrodes for the described measurement is shown in this figure (see also table 1). The curve corresponds to the potential performance during the inventive method whereby step a. indicates the cleaning cycle (i.e., electrochemical reduction), step b. is the holding step (interaction of intermediates on the working electrode) and step c. shows the analyzing scan for the evaluation of the stabilizer concentration (i.e., measurement of the Faradaic current).

A schematic description in terms of a potential-time curve of steps a. (only electrochemical reduction) to c. is shown in FIG. 1.

The Faradaic current describes currents derived from processes which follow Faraday's law, i.e., processes where electrons or ions cross the electrolyteelectrode interfaces and wherein these charge transfer steps are accompanied by oxidation reactions at the anode and reduction reactions at the cathode. The Faradaic current can be divided in a) a non-stationary Faradaic current which resembles a time dependent mass transport (e.g., the electrolyte and/or the working electrode is not agitated during a voltammetric measurement) and b) a stationary Faradaic current which resembles a time independent mass transport (e.g., the electrolyte and/or the electrode is agitated during a voltammetric measurement).

The term 'interaction' is defined herein by phenomena observed between the electrolyte and the surface of the working electrode and includes adsorption (chemisorption and physisorption) and partial charge transfer.

The term 'intermediate species' is defined herein as molecules and ions part of the electroless metal or metal alloy plating electrolyte which interact with the surface of the working electrode. Such intermediate species include the stabilizer additive(s), molecules and/or ions derived thereof in the electrolyte or during use of said electrolyte, the reducing agent and molecules and/or ions derived thereof in the electrolyte or during use thereof, metal ions and/or complexes of metal ions and/or complexes between stabilizer additive(s) and reducing agent.

In one embodiment of the present invention, the sample of said electroless metal or metal plating electrolyte is taken from a metal plating electrolyte and transferred to a stabilizer additive control set-up as described below.

In another embodiment of the present invention, the sample of said electroless metal or metal alloy plating electrolyte is taken automatically from the plating electrolyte and transferred to a stabilizer additive control stet-up as described below by techniques known to the person skilled in the art.

In still another embodiment of the present invention, a sample of said electroless metal or metal alloy plating electrolyte is taken and the voltammetric measurement of the stabilizer additive concentration in accordance with steps a. to d. and optional steps e. and f. is performed in an online mode providing real time control of stabilizer additives in electroless plating electrolytes.

Step a. of the inventive method is necessary to enable reproducible conditions for individual measurements. The working electrode surface is treated in step a. prior to the measurement of the stabilizer additive concentration in order to provide a clean and pure metallic surface free of oxides, sulfides and organic residues. Methods for said purpose are known in the art. For example, a chemical etching treatment of the working electrode can be done in a persulphate-based etch cleaner. Such cleaners are known in the art. The electrochemical reduction of oxidized metal species on the metal working electrode surface is feasible by treating said surface with a cleaning cycle in the cathodic potential regime using a three electrode set-up described below. In a preferred embodiment of the present invention, a copper working electrode is conditioned prior to stabilizer additive measurement by treating said electrode first in a chemical etching solution and then applying an electrochemical reduction procedure. The electrochemical reduction of the working electrode can be done for example by applying a cleaning step with a potential of −1.5 V (versus Ag/AgCl) in the electroless metal or metal alloy plating electrolyte. In case of a noble metal working electrode, e.g., a platinum working electrode the conditioning step a. may consist only of a removal of residues such as grease, oils and fingerprints. Such procedures are referred herein as cleaning.

In general, at least one method selected from chemical etching, electrochemical reduction or cleaning is applied during step a. However, two ore more of said methods may be combined throughout step a. in different order. In another embodiment, only a electrochemical reduction of the working electrode is applied in step a. Such an electrochemical reduction may be done in the electroless metal or metal alloy plating electrolyte.

Suitable working electrode materials are selected from the group, comprising copper, nickel, platinum, gold, silver, palladium and glassy carbon.

Differently shaped working electrodes can be used for the inventive method including plate shaped electrodes, rings, ribbons, discs and wires.

Either the electroless metal or metal alloy plating electrolyte or the working electrode can be independently agitated during step c. or used without agitation for said purpose.

The intermediate species present in the electroless plating electrolyte are interacting during step b. with the surface of the working electrode. Therefore, a potential of for example in case of an electroless copper plating electrolyte −0.6 V (versus Ag/AgCl) is applied to the working electrode and held for a time required to reach a steady state of the interaction of intermediate species with the working electrode surface.

The Faradaic current is measured in step c. in order to determine the concentration of the stabilizer additive or mixture of stabilizer additives. It is possible to measure the stationary or non-stationary Faradaic current. The Faradaic current correlates with the concentration of the stabilizer additive and/or mixture of stabilizer additives. In one embodiment of the present invention, the Faradaic current of the reducing agent is measured in step c. Step c. comprises a potential cycle starting from the potential defined in step b. and scanning into cathodic direction. In general, the analyzing scan can go from a start potential to an end potential or from a start potential to an end potential and from there back to said start potential.

Figure 2:
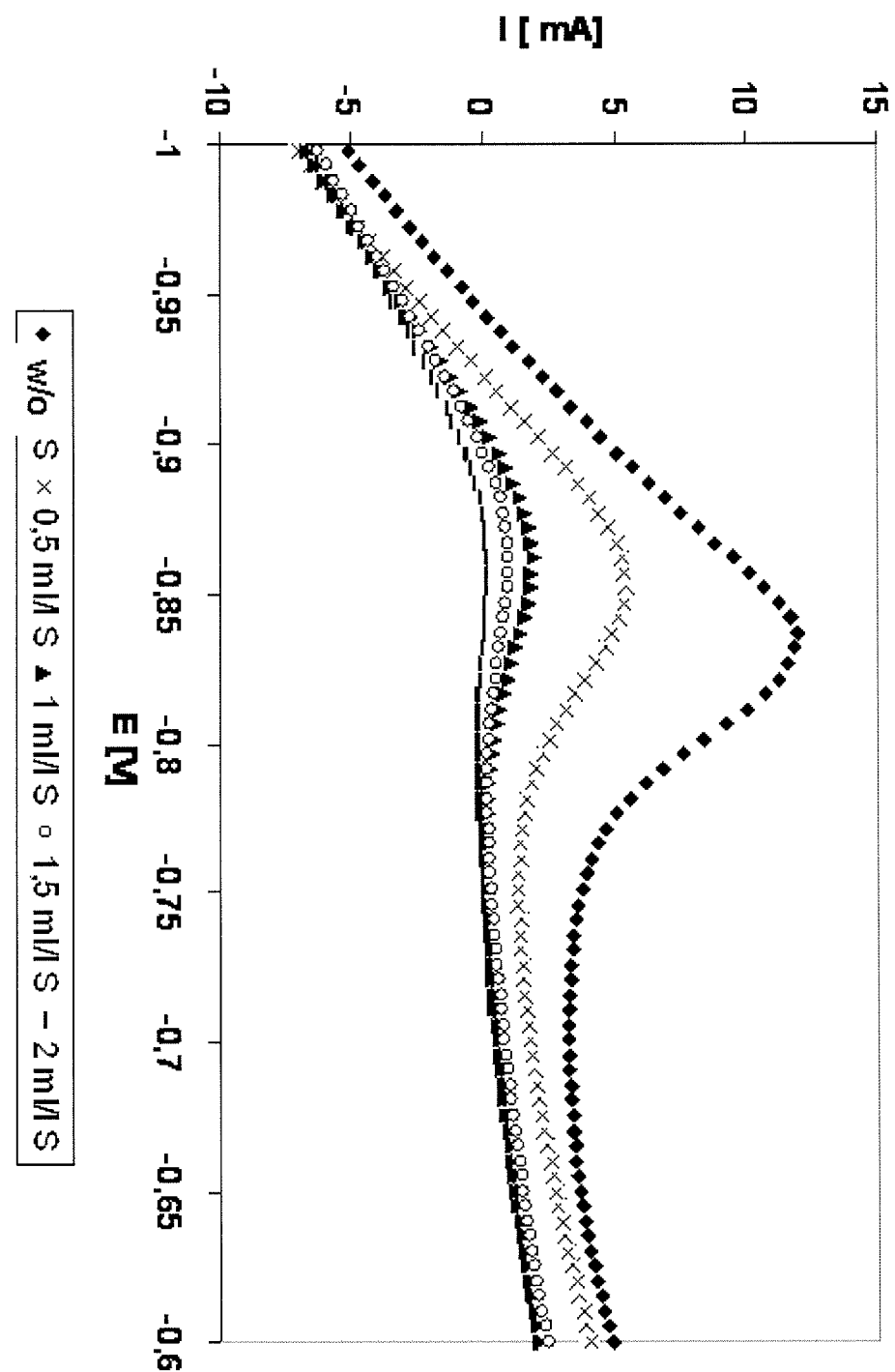
FIG. 2 shows the influence of the stabilizer additive mixture concentration on the Faradaic current as a function of the electrode potential in the electroless copper plating electrolyte used in example 1. The individual data traces differ in their stabilizer additive concentration, which ranges from 0 to 2 ml/l.

In step d., the measured Faradaic current is determined. This is for example shown in FIG. 2, where for a number of potential values E the corresponding Faradaic current values of the potential scan is provided. Preferably, a potential range is selected wherein the differences of Faradaic current values from different stabilizer additive concentrations are biggest. In FIG. 2, this is the case for potential values E in the range of −0.9 to −0.8 V.

In one embodiment of the invention, a three electrode set-up with a Ag/AgCl reference electrode, a platinum counter electrode and a copper working electrode and a potentiostat can be used to control the concentration of the stabilizer additive or mixture of stabilizer additives in an electroless metal or metal alloy plating electrolyte. During said control, the electrolyte and working electrode can be independently agitated or not agitated.

The inventive method for control of stabilizer additives, more specifically steps b and c can be performed for example at the temperature at which the electrolyte is held during metal or metal alloy deposition in production scale. In general, the inventive method is applicable in a temperature range of 10 to 100° C., more preferred between 15 and 60° C. and most preferred between 20 and 40° C. On the other hand, the temperature during steps b. and c. in a series of individual measurements has to be kept constant with a deviation of ≤+/−5° C., more preferred of ≤+/−2° C., most preferred ≤+/−1° C. around the selected measurement temperature in order to provide reproducibility of the resulting data.

The determined value of the Faradaic current of an electroless metal or metal plating electrolyte is optionally compared with the target value of the Faradaic current. The target value is equal to the Faradaic current of a freshly prepared electroless metal or metal alloy plating electrolyte determined with the inventive method. A freshly prepared electroless metal or metal alloy plating electrolyte contains one or more stabilizer additives in an amount which resembles optimal operating conditions of said electrolyte, e.g., no undesired precipitation of components present in the plating electrolyte, desired plating speed and desired properties of the metal or metal alloy deposit.

In case of a deviation of the determined Faradaic current value from the target Faradaic current value, stabilizer additive or mixture of stabilizer additive is added to the tested electroless plating electrolyte.

The target value should be matched after addition of said stabilizer additive or mixture to a used plating electrolyte. In case of an observed deviation from the Faradaic current target value, the stabilizer additive or mixture of stabilizer additives is added to the working plating electrolyte in an amount sufficient to reach the target value.

The inventive method can also be used as an on-line method: at first a sample is taken automatically from the plating electrolyte of a production line for electroless metal deposition. In case of an electroless copper deposition, $Cu^{2+}$, NaOH and formaldehyde concentrations are determined and replenished to set point for this sample (i.e., concentrations for best mode of operation of the plating electrolyte).

Then the solution has to be heated or cooled to working electrolyte conditions (e.g., 30° C.). A Ag/AgCl reference electrode, a platinum counter electrode and a copper working electrode in a fixed, classical 3-electrode arrangement are applied for this measurement. The copper working electrode is a disposable electrode and has to be renewed and pre cleaned before each measurement. The technical application of a disposable copper electrode in an online measurement environment is not described here, since it is a commonly known method.

Steps a. to d. are done automatically and the collected data are stored.

In order to deliver a working dosing concept, the information of the determined Faradaic current value, i.e., the stabilizer additive concentration is transferred to the controlling unit of the production line. The lacking amount of stabilizer additive solution is calculated and dosed immediately into the production plating electrolyte.

EXAMPLES

A three electrode test set-up with a PGSTAT 30 potentiostat (Autolab) and GPES software was used for control of stabilizer additives in electroless copper plating electrolytes in examples 1 to 3. All measurements were done with a Ag/AgCl reference electrode (Metrohm) and a platinum wire as the counter electrode. The electrolyte temperature was held at 30° C. (+/−2° C.) during all measurements. The copper working electrodes were treated with a sodium-persulphate based etch cleaner (150 g/l sodium-persulphate, 5 g/l $Cu^{2+}$ and 35 ml/l of 50 wt-% $H_2SO_4$) at room temperature for 30 s prior to use.

The electroless copper electrolyte used for examples 1 to 4 comprised
2 g/l $Cu^{2+}$
10 g/l NaOH
5 g/l formaldehyde (reducing agent)
20 g/l tartrate (complexing agent)
Different types and amounts of stabilizer additives were added to said electrolyte during examples 1 to 4.

Example 1

The stabilizer additives of an electroless copper electrolyte were monitored. A copper plate (10×40 mm) was used as the working electrode. Both, working electrode and electrolyte were not agitated during steps a.-c. (table 1).

0 to 2 ml/l of a proprietary stabilizer additive mixture (Printoganth® PV, a product of Atotech Deutschland GmbH), comprising organic and inorganic sulphur compounds and organic nitrogen compounds were added to the electroless copper electrolyte. No cyanide ions were present in the stabilizer additive mixture.

The test protocol used for the control of the stabilizer additive mixture is summarized in table 1:

| Step | | Potential [V] versus Ag/AgCl reference electrode | Remarks |
|---|---|---|---|
| a. | Conditioning of working electrode: 1. chemical etching 2. electrochemical reduction | −1.5 | → reproducible working electrode surface Na-persulphate based etch cleaner Reduction of $Cu^{x+}$ to $Cu^0$ |
| b. | interaction of intermediates on working electrode surface | −0.6 | 10 min at fixed potential |
| c. | Analyzing; scan 40 mV/s scan speed | −0.6 −1.2 −0.6 | Measurement of non-stationary Faradaic current [mA] |

The analyzing scan (step c. in table 1) is shown as a current vs. potential plot in FIG. 2. The figure shows the forward scan of the analyze cycle c. (−1000 mV to −600 mV) for different stabilizer additive mixture concentrations in the range of 0 to 3 ml/l. At a potential of −850 mV one can see a depression of the Faradaic current values with an increase of the stabilizer additive mixture concentration. The coverage of the working electrode with stabilizer components depends on the concentration of stabilizer components in the plating electrolyte.

Example 2

The cyanide ion stabilizer additive of an electroless copper plating electrolyte was monitored. A copper plate (10×40 mm) was used as the working electrode. Both, working electrode and electrolyte were not agitated during steps a.-c. (table 1).

The cyanide ion stabilizer additive concentration was varied between 0 and 20 ppm.

The test protocol used was similar to the one shown in table 1, but instead of measuring the anodic oxidation current of the reducing agent formaldehyde in step c., now the cathodic reduction current of formaldehyde and/or its intermediate species with cyanide ion stabilizer additive was monitored in step c.

Figure 3:
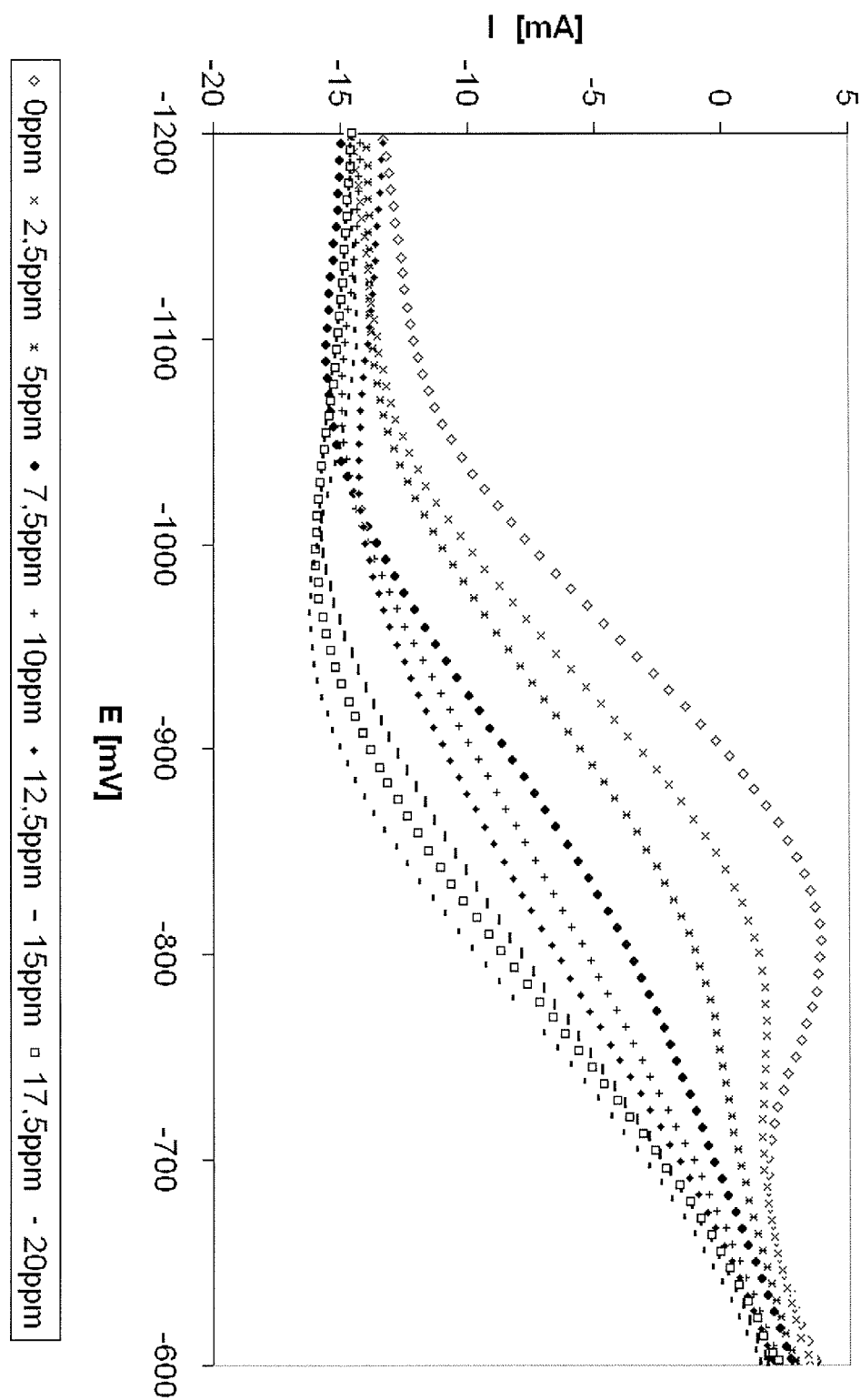
FIG. 3 shows the results obtained in example 2 wherein numerous concentrations of the cyanide ion stabilizer additive in the electroless copper plating electrolyte were recorded in the range between 0 ppm and 20 ppm.

The results of the analyzing scan (step c.) are shown in FIG. 3. The impact of different cyanide ion stabilizer additive concentrations on the current/potential curves is clearly visible. Therefore, also the cyanide ion stabilizer additive can be monitored using the inventive method.

Example 3

Figure 4:
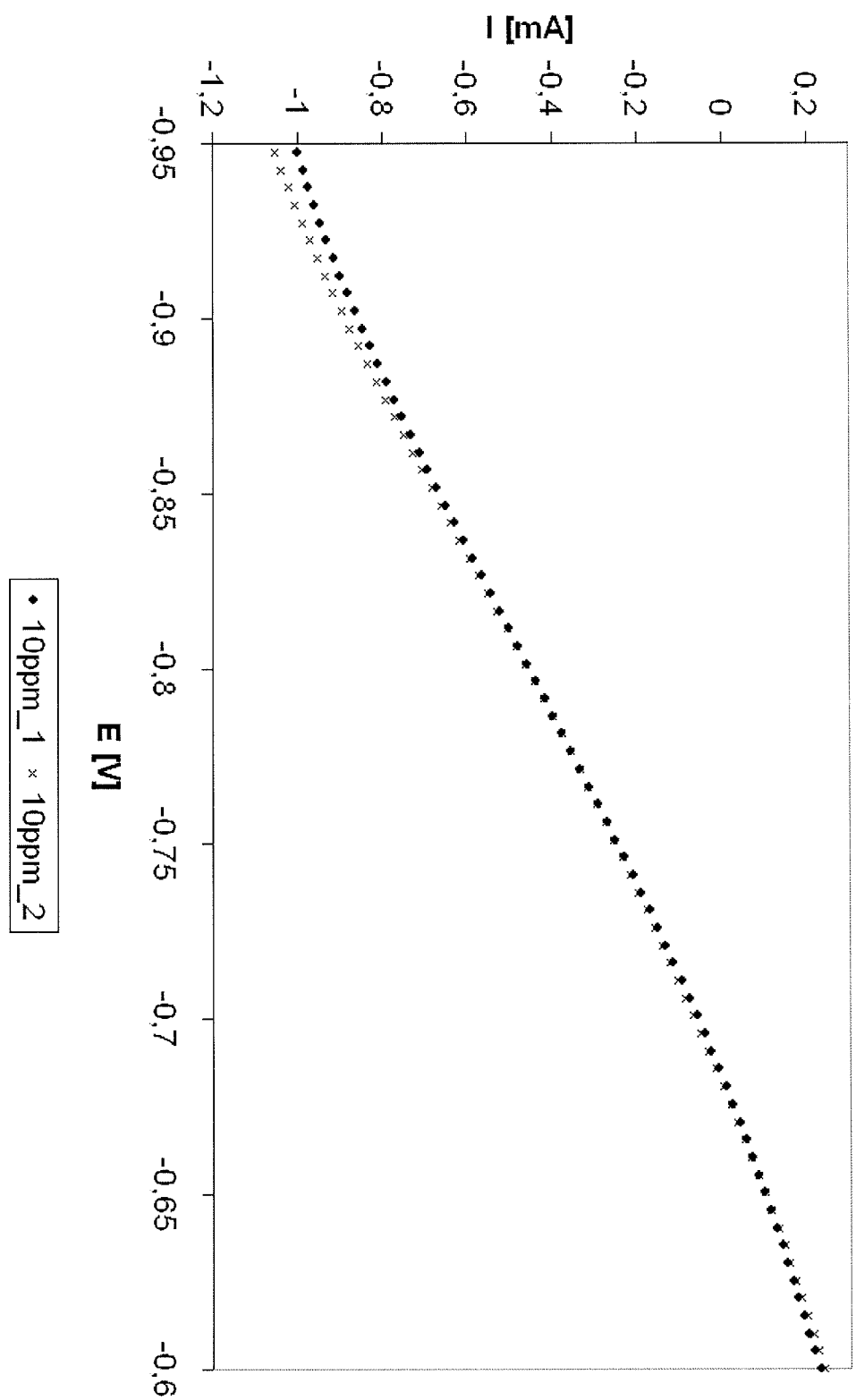
FIG. 4: In this figure two samples of an electroless copper plating electrolyte with a concentration of 10 ppm cyanide ions as the stabilizer additive were measured to check the reproducibility of the inventive method (example 3). Each measurement was carried out with a fresh make up of the copper plating electrolyte. Whereby 10 ppm__1 is the first and 10 ppm__2 is the second measurement with the same amount of the cyanide ion stabilizer additive.

The reproducibility of the inventive method was investigated. To two portions of the electroless copper plating electrolyte stock solution 10 ppm of cyanide ions were added each and the test protocol shown in table 1 applied. The resulting current/potential curves for both samples are shown in FIG. 4. Both individual curves match almost completely. Therefore, the inventive method is reproducible.

Example 4

Comparative Experiment

Figure 5:
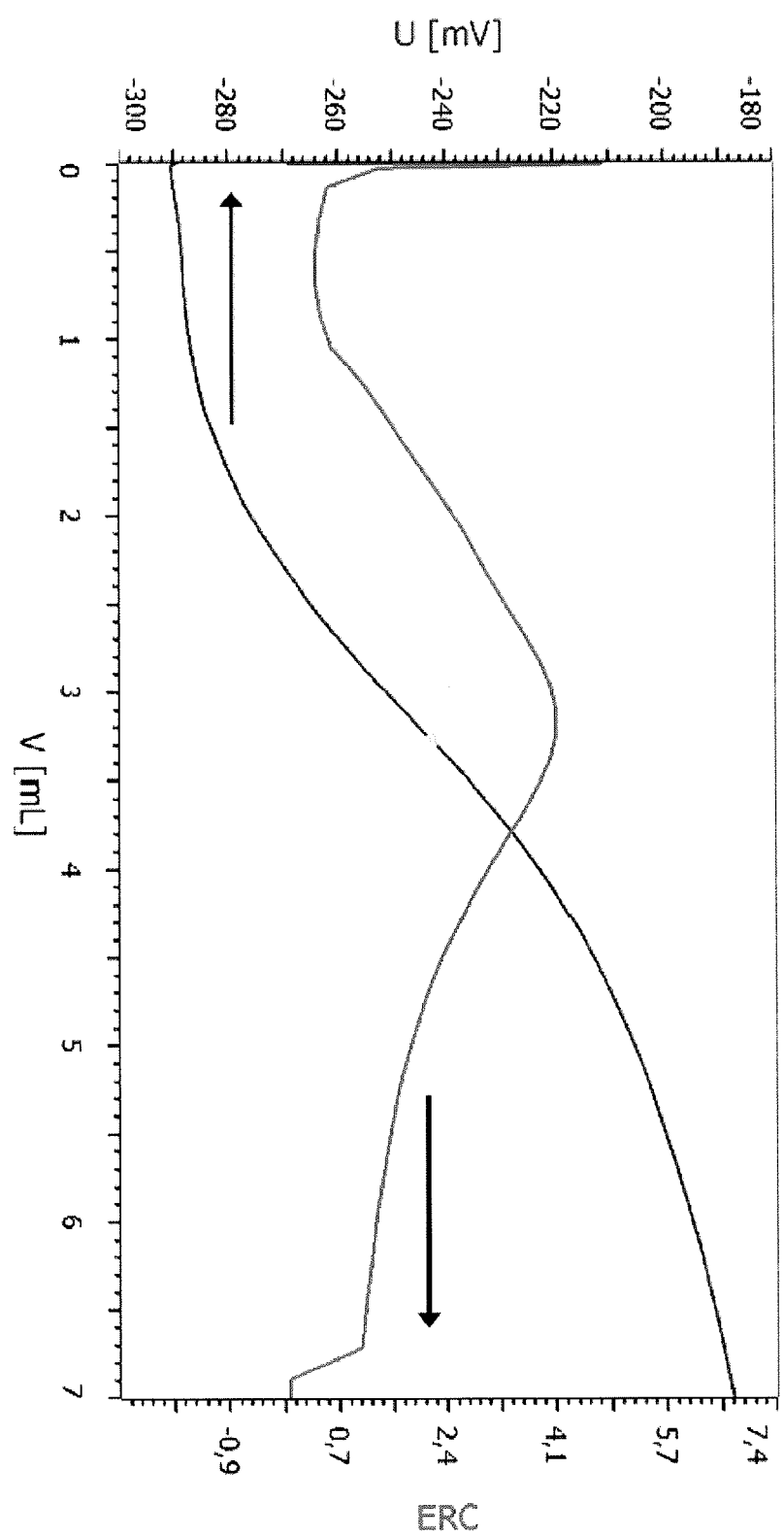
FIG. 5 shows the titration curve (potential U versus spent volume of AgCl solution V and the first derivation of U (ERC) versus spent volume V of AgCl solution) obtained from an electroless copper plating electrolyte containing 10 ppm cyanide ions as the stabilizer additive and no formaldehyde (comparative example 4). The titration curve shows a clear point of inflection leading to the right cyanide ion concentration.

For comparison, the cyanide ion concentration in an electroless copper electrolyte described in example 2 was monitored by a potentiometric titration with $AgNO_3$ using a cyanide ion sensitive electrode (measurement of the potential versus a Ag/AgCl reference electrode). This method yielded sufficient precise results for cyanide ion concentrations in the range of 0 to 20 ppm as long as no formaldehyde (i.e., reducing agent) was present in the electroless copper electrolyte (FIG. 5).

Figure 6:
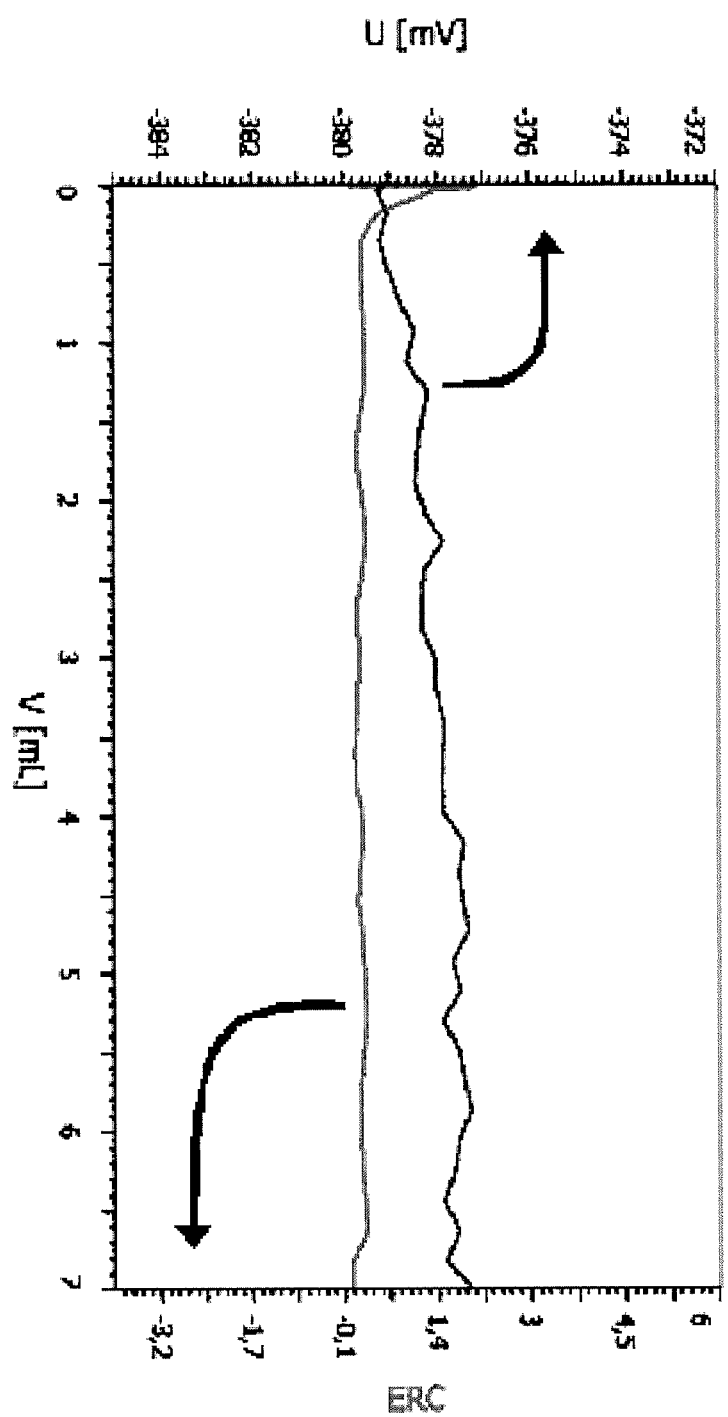
FIG. 6 shows the titration curve (potential U versus spent volume of AgCl solution V and the first derivation of U (ERC) versus spent volume V of AgCl solution) obtained from an electroless copper electrolyte containing 10 ppm cyanide ions as the stabilizer additive and formaldehyde as the reducing agent (comparative example 4). The titration curve shows no point of inflection and therefore, the cyanide ion concentration can not be obtained from such a measurement.

No reproducible results for cyanide ion concentrations were obtained with an electroless copper electrolyte used in example 2, i.e., in the presence of the reducing agent formaldehyde (FIG. 6).

Example 5

To prove the capability of the inventive method for stabilizer additive control a hypophosphite electroless copper plating electrolyte was investigated. The test was done with a copper plate working electrode (10×40 mm).

The composition of the electroless copper plating electrolyte was:

| | | |
|---|---|---|
| 1 g/l | $Cu^{2+}$ | |
| 0.2 g/l | $Ni^{2+}$ | |
| 9 g/l | Tri sodium citrate | |
| 15 g/l | Boric acid | |
| 9 g/l | NaOH | |
| 27 g/l | Sodium hypophosphite (reducing agent) | |
| 0.5 to 2.5 ml/l | proprietary stabilizer additive mixture (Printoganth ® FF, a product of Atotech Deutschland GmbH) | |

The overall measurement conditions for this test were the same like for the other tests (table 1). For every measurement a new make up of the electro less copper plating electrolyte was done.

Figure 7:
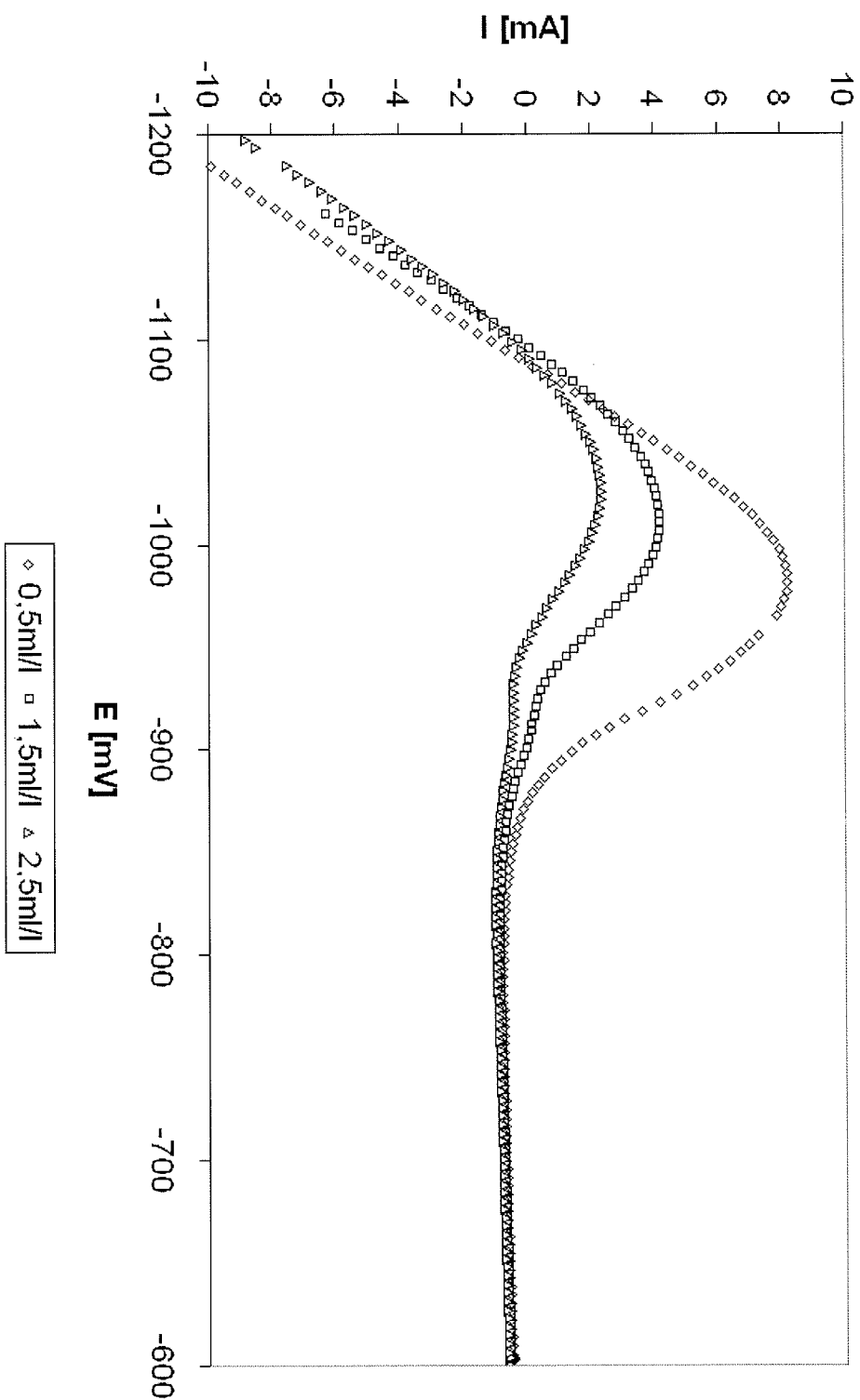
FIG. 7 shows the results obtained from the analyzing scan (step c.) in example 5 wherein the concentration of the stabilizer additive mixture was varied between 0.5 and 2.5 ml/l.

The potential-current curves for the three different stabilizer concentrations are clearly distinctive (FIG. 7). The oxidation of the reducing agent sodium hypophosphite occurred between −900 and −1100 mV.

Example 6

Figure 8:
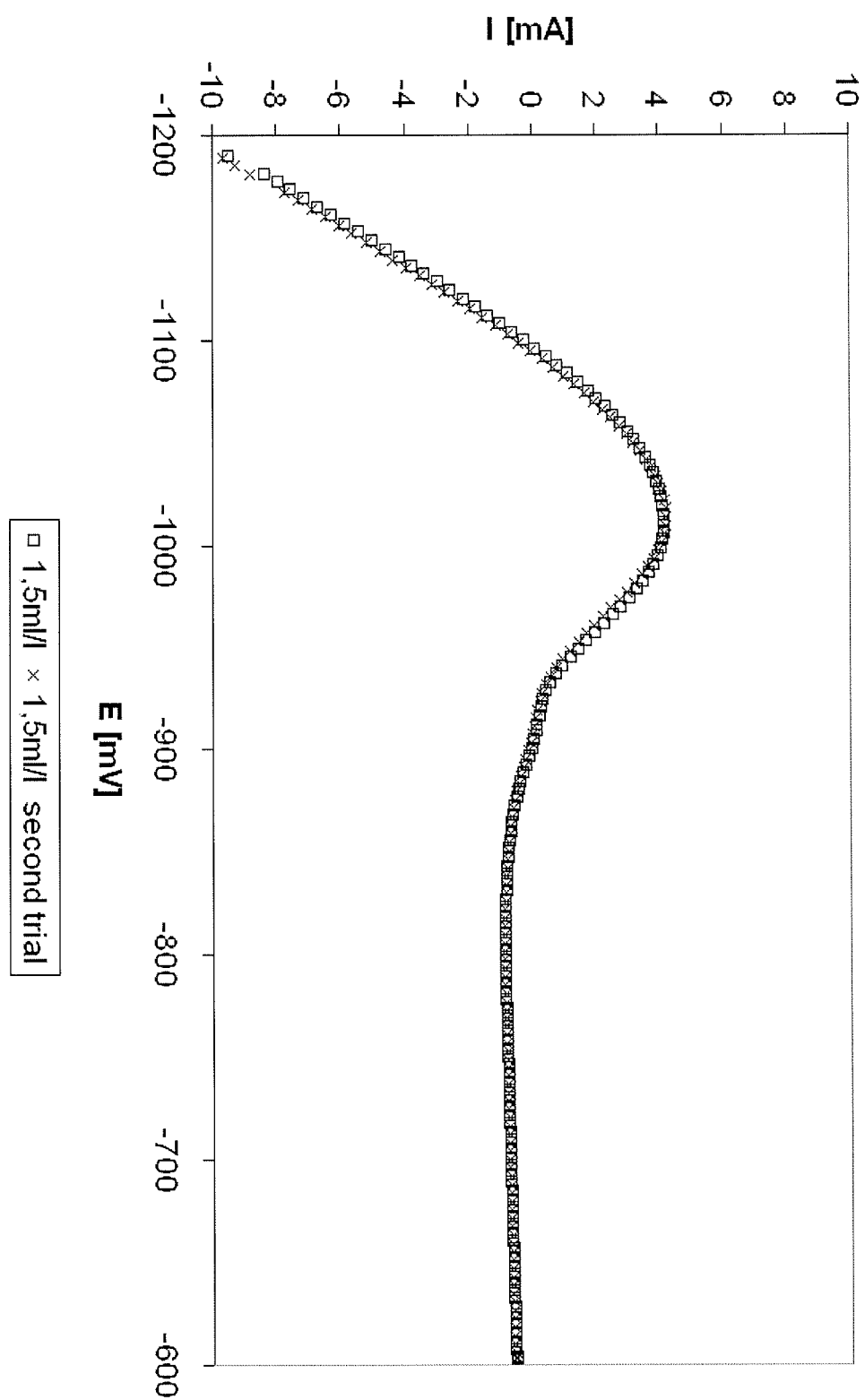
FIG. 8 shows the analyzing scans (step c.) derived from a hypophosphite based electroless copper plating electrolyte. Two times the same concentration of the stabilizer additive mixture was measured (example 6). The diagram shows two identical scans of potential/current curves for both individual measurements, i.e., plating electrolyte make-ups.

The reproducibility of the inventive method was investigated. To two portions of the hypophosphite based electroless copper plating electrolyte stock solution from example 6, 1.5 ml/l of the stabilizer additive mixture was added each and the test protocol shown in table 1 applied. The resulting current/potential curves for both samples are shown in FIG. 8. Both individual curves match almost completely. Therefore, the inventive method is reproducible.

Example 7

For an electroless nickel plating electrolyte the same method was applied to prove its capability. The test was carried out with a nickel plated copper electrode (size: 10×40 mm).

The electro less nickel electrolyte was composed of:

| | | |
|---|---|---|
| 3 g/l | $Ni^{2+}$ | |
| 15 g/l | Sodium hypophosphite (reducing agent) | |
| 0.5-1.5 ml/l | proprietary stabilizer additive mixture (Adhemax ® ALF, a product of Atotech Deutschland GmbH) | |

Furthermore a mixture of complexing agents and NaOH to adjust a pH value of 6.5 was added. The test method was the same like for the other tests (table 1) except the use of a nickel plated copper working electrode instead of a copper working electrode. Three different stabilizer additive mixture concentrations were measured (0.5, 1 and 1.5 ml/l).

Figure 9:
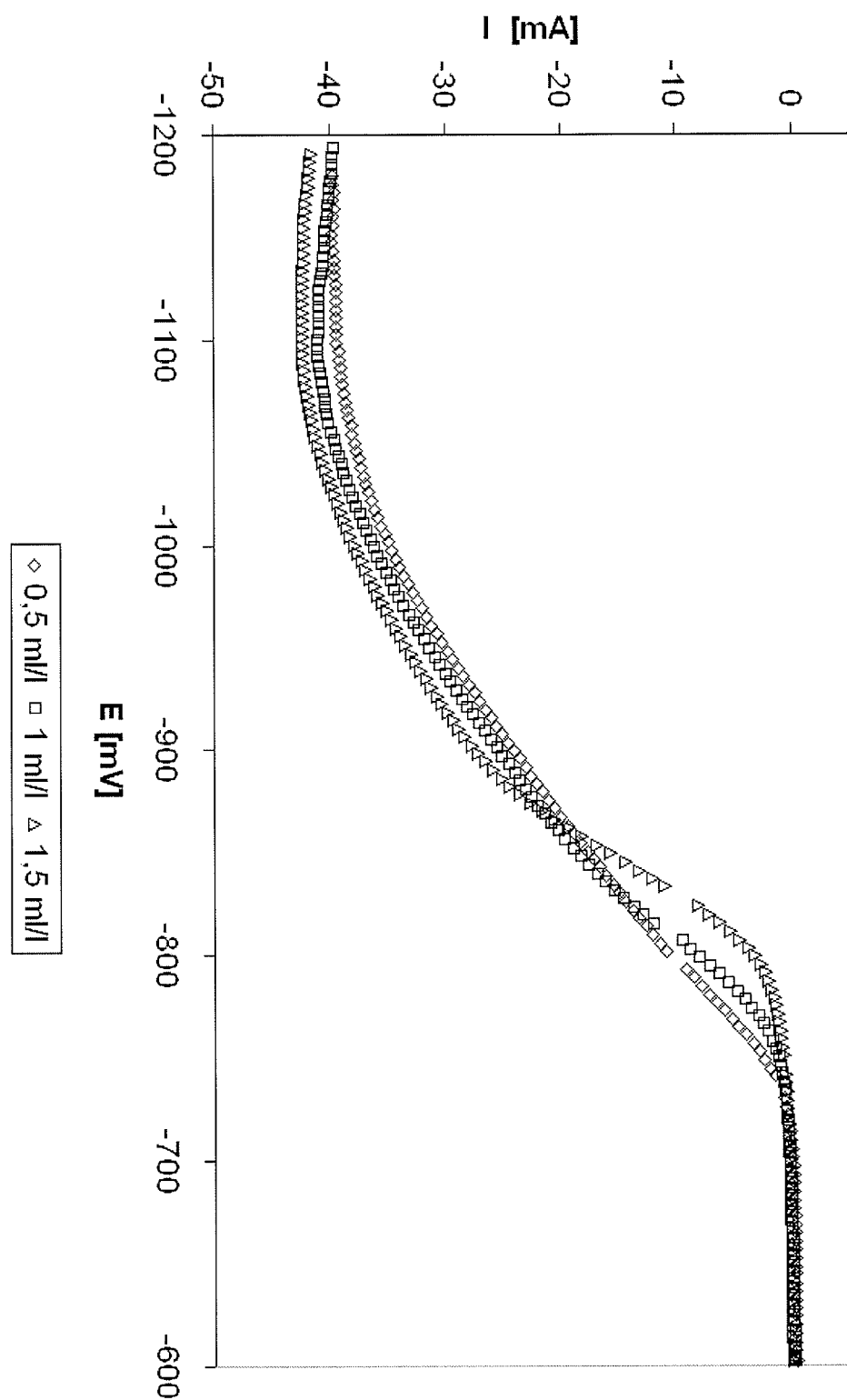
FIG. 9 shows the analyzing scan (step c.) from a hypophosphite based electroless nickel plating electrolyte (example 7). The suitable potential range for the analyze cycle is between −750 and −850 mV. Every trial was done with a new make up of the electro less Nickel bath.

The results are shown in FIG. 9. The data evaluation showed distinctive values for the potential/current curves in a potential range between −750 and −850 mV for different stabilizer additive mixture concentrations.

Example 8

Figure 10:
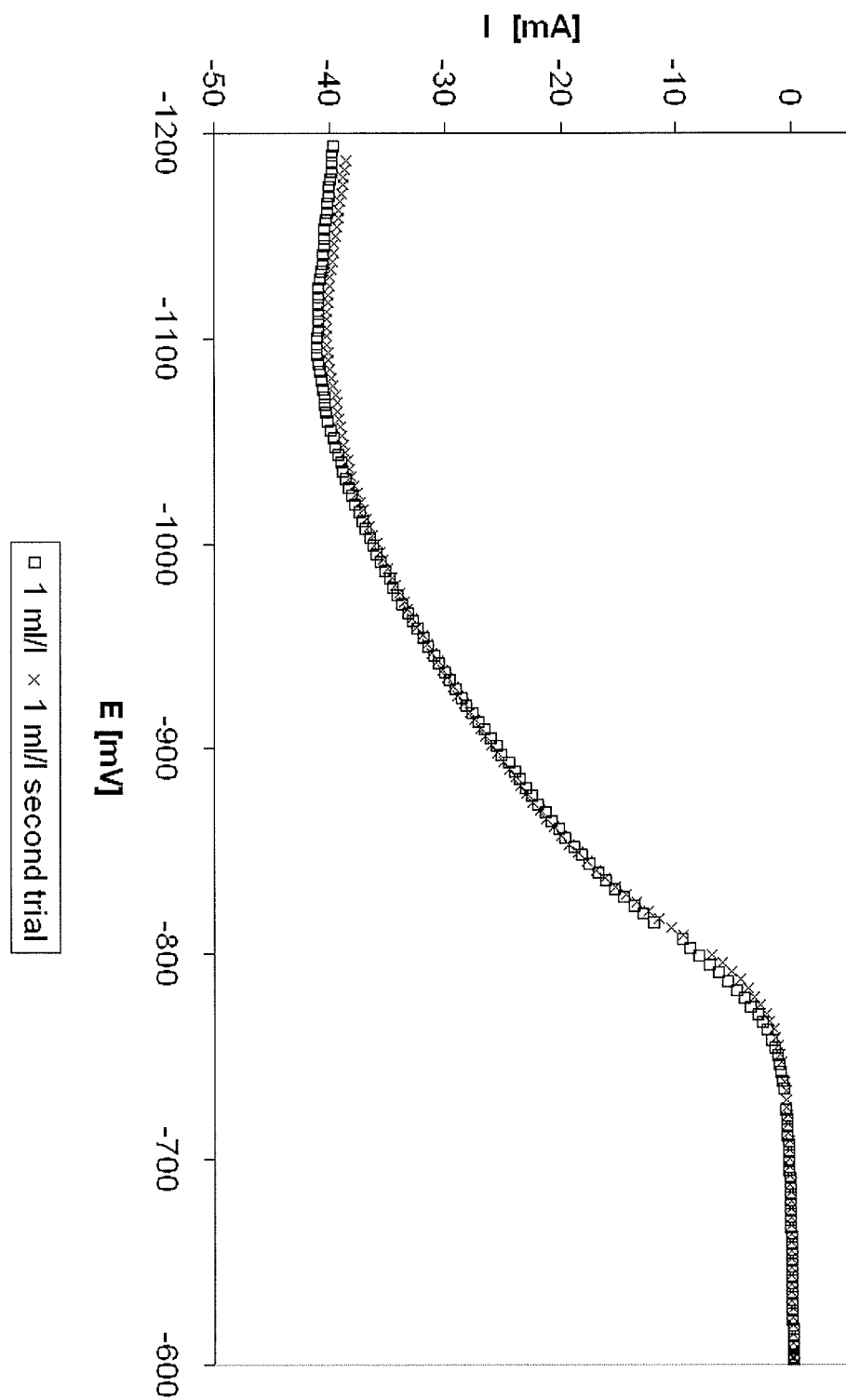
FIG. 10: shows the analyzing cycles (step c.) derived from a hypophosphite based electroless nickel plating electrolyte. Two times the same concentration of the stabilizer additive mixture was measured (example 8). The diagram shows two identical scans of potential/current curves for both individual measurements, i.e., plating electrolyte make-ups.

The reproducibility of the inventive method was investigated. To two portions of the hypophosphite based electroless nickel plating electrolyte stock solution from example 8, 1 ml/l of the stabilizer additive mixture was added each and the test protocol shown in table 1 applied. The resulting current/potential curves for both samples are shown in FIG. 10. Both individual curves match almost completely. Therefore, the inventive method is reproducible.

The invention claimed is:

1. A voltammetric method for the measurement of the stabilizer additive concentration in electroless metal or metal alloy plating electrolytes, comprising the following steps:
   a. conditioning of the working electrode surface b. thereafter bringing into contact such working electrode surface with the electroless metal or metal alloy plating electrolyte and applying a fixed potential in a three-electrode set-up to said working electrode surface for a time required to reach a steady state of the interaction of intermediate species with the working electrode surface c. measuring the Faradaic current by applying a potential scan starting from the fixed potential applied during step b d. determining of at least one Faradaic current value at at least one potential value of a potential scan, wherein stabilizer additives are added to the electroless metal or metal plating electrolyte in order to obtain the target value, if a deviation of the determined Faradaic current from the target Faradaic current is observed.

2. The method according to claim 1, wherein the determined Faradaic current is compared with the target Faradaic current.

3. The method of claim 1, wherein the working electrode surface is conditioned by an electrochemical reduction in the electroless metal or metal alloy plating electrolyte.

4. The method according to claim 1, wherein the working electrode is chemically etched prior to the electrochemical reduction.

5. The method according to claim 1, wherein the determined Faradaic current is a stationary Faradaic current.

6. The method according to claim 1, wherein the determined Faradaic current is a non-stationary Faradaic current.

7. The method according to claim 1 wherein the Faradaic current measured in step c is an oxidation current.

8. The method according to claim 1 wherein the Faradaic current measured in step c is a reduction current.

9. The method according to claim 1 wherein a first Faradaic current is measured in step c is a reduction current and a second Faradaic current measured in step c is an oxidation current.

10. The method according to claim 1, wherein the electroless metal or metal alloy plating electrolyte is a chemical plating electrolyte applying a reducing agent.

11. The method according to claim 1, wherein the electroless metal or metal alloy plating electrolyte is an immersion plating electrolyte.

12. The method according to claim 1, wherein the electroless metal or metal alloy plating electrolyte is selected from the group comprising copper, nickel, gold, palladium, ruthenium, tin, silver and alloys thereof.

* * * * *